US00PP28890P2

(12) United States Plant Patent
Wood

(10) Patent No.: US PP28,890 P2
(45) Date of Patent: Jan. 23, 2018

(54) ***POTENTILLA* PLANT NAMED 'SMPFMY'**

(50) Latin Name: *Potentilla fruticosa*
Varietal Denomination: SMPFMY

(71) Applicant: Timothy Wood, Spring Lake, MI (US)

(72) Inventor: Timothy Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 15/330,924

(22) Filed: Nov. 14, 2016

(51) Int. Cl.
*A01H 5/02* (2006.01)

(52) U.S. Cl.
USPC ..... Plt./237

(58) Field of Classification Search
USPC ..... Plt./237
CPC ..... A01H 5/0216
See application file for complete search history.

*Primary Examiner* — Kent L Bell
(74) *Attorney, Agent, or Firm* — Cassandra Bright

(57) ABSTRACT

A new and distinct *Potentilla* cultivar named 'SMPFMY' is disclosed, characterized by, good mildew resistance, large, strong yellow flowers and continuous blooming. The new variety is a *Potentilla*, normally produced as an outdoor garden or container plant.

2 Drawing Sheets

Latin name of the genus and species: *Potentilla fruticosa*.
Variety denomination: 'SMPFMY'.

BACKGROUND OF THE INVENTION

The new *Potentilla* cultivar is a product of a planned breeding program conducted by the inventor, Timothy D. Wood, in Grand Haven, Mich. The objective of the breeding program was to produce new *Potentilla* varieties with continuous blooming and strong flower colors that resist fading. The open pollination resulting in this new variety was made during July of 2010.

The new *Potentilla* 'SMPFMY' resulted from an open pollination with several different *Potentilla fruticosa* plants as both seed parents and pollen parents. Both exact seed and pollen parent are unknown. The new variety was identified as a potentially interesting selection in June of 2013, at a nursery in Grand Haven, Mich.

Asexual reproduction of the new cultivar 'SMPFMY' by softwood cuttings was first performed during June of 2013, at commercial greenhouse in Grand Haven, Mich. Subsequent propagation has shown that the unique features of this cultivar are stable and reproduced true to type in three successive generations.

SUMMARY OF THE INVENTION

The cultivar 'SMPFMY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMPFMY' These characteristics in combination distinguish 'SMPFMY' as a new and distinct *Potentilla* cultivar:

1. Large, bright yellow flowers.
2. Strong yellow flower color.
3. Very good foliar mildew resistance.
4. Continuous blooming plants.

PARENT COMPARISON

Parent varieties cannot be confirmed.

COMMERCIAL COMPARISON

Plants of the new cultivar 'SMPFMY' can be compared to the commercial variety *Potentilla fruticosa* 'Lundy', U.S. Plant Pat. No. 22,176. These varieties are similar in most horticultural characteristics, however, 'SMPFMY' differs in the following:

1. Plant habit of the new variety is more upright than the round, mounded habit of 'Lundy'.

BRIEF DESCRIPTION OF THE PHOTOGRAPHS

Figure 1:
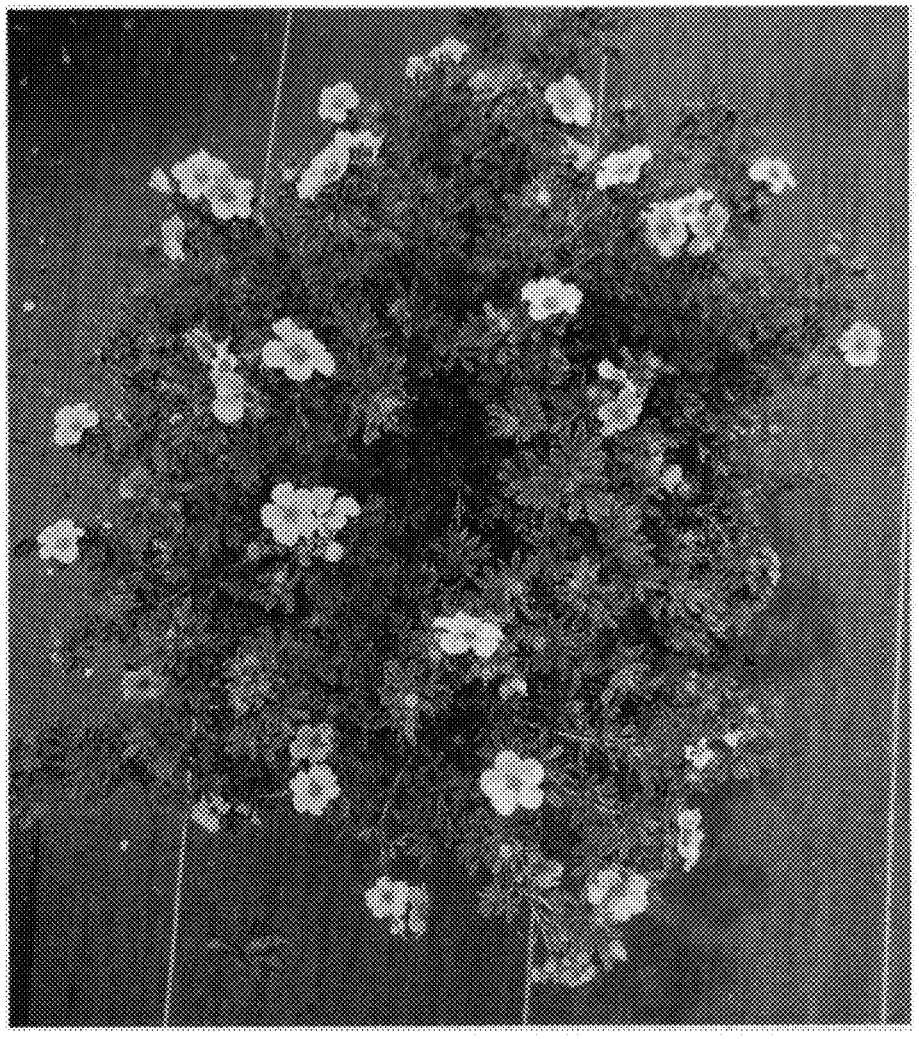

The accompanying photograph in FIG. 1 illustrates in full color a flowering plant of 'SMPFMY' in the Summer.

Figure 2:
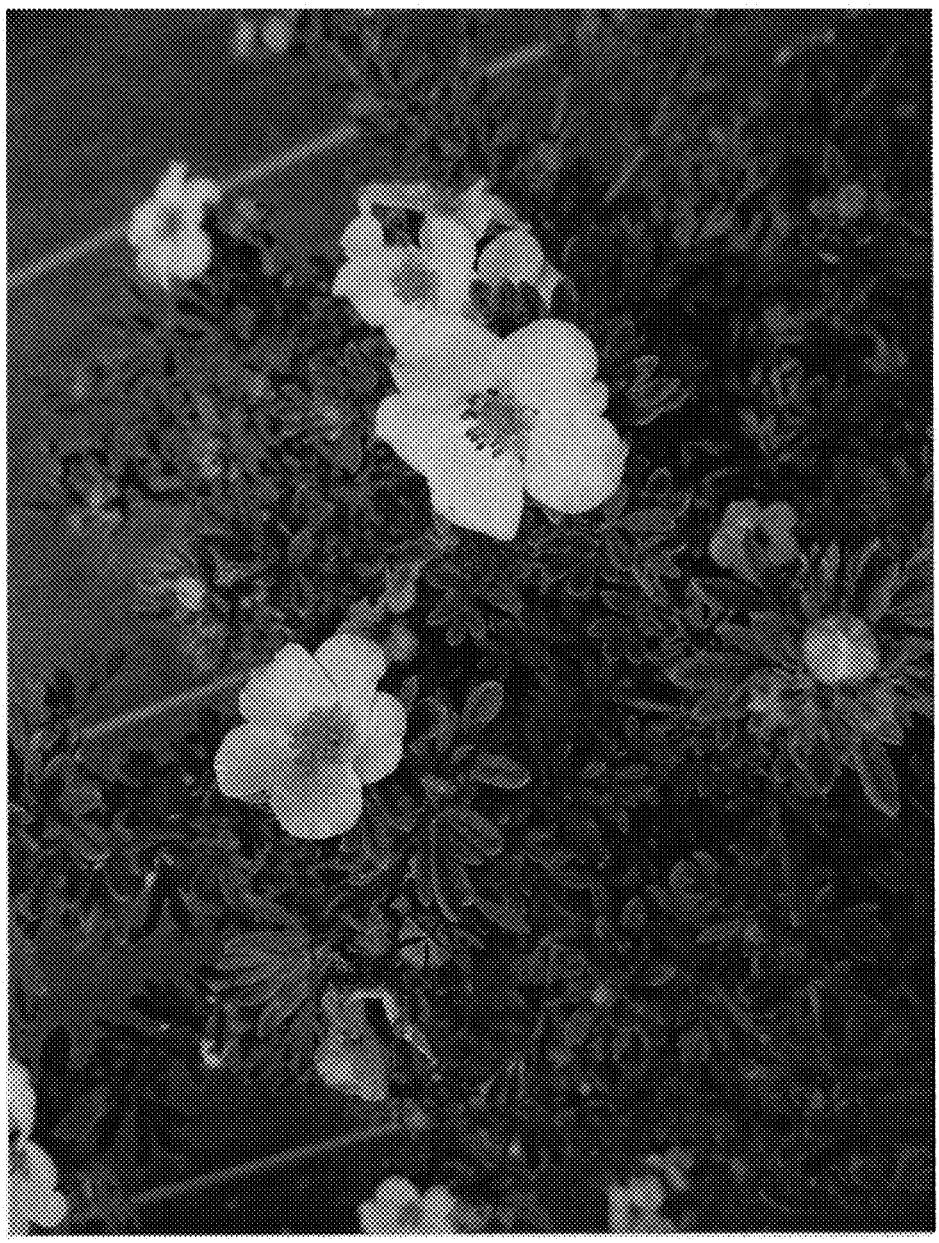

FIG. 2 illustrates a closer view of the flower. Plants were grown outdoors in Grand Haven, Mich., in a field setting. Age of the plant photographed is approximately 2 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'SMPFMY' plants grown in a polyhouse in Grand Haven, Mich. Plants were described during June. The plants were approximately 2 years old grown in 2 gallon containers. The growing temperature ranged from 18° C. to 27° C. during the day, and 5° to 10° C. at night. Measurements and numerical values represent averages of typical plant types.

Botanical classification: *Potentilla fruticosa* 'SMPFMY'.

PROPAGATION

Time to initiate roots: About 20 days at approximately 24° C.
Root description: Moderately dense, fibrous, freely branching. Colored white and brown, not accurately identified with R.H.S. chart.
Time to produce a young rooted plant: About 60 days at 24° C.

PLANT

Plant type: Perennial shrub.
Age of plant described: Approximately 2 years old.
Growth habit: Upright and rounded.
Pot size of plant described: 2 gallon pot.
Height: Approximately 38 cm.
Plant spread: Approximately 55 cm.
Growth rate: Moderate.
Plant vigor: Good.
Branching characteristics: Free branching, enhanced with pinching.
Length of primary lateral branches: Approximately 22.0 cm.
Diameter of lateral branches: Approximately 1.5 mm.
Quantity of lateral branches: 21.
Stem:
*Aspect/angle.*—35° to 75°.
*Strength.*—Strong.
*Stem pubescence.*—New growth pubescent, older growth woody.
*Stem color.*—Near RHS Yellow-Green 145B, woody growth near Brown 200B.
Internode length: Average 2.0 cm.

FOLIAGE

Arrangement: Alternate; palmately compound with three to five leaflets per leaf. Leaflets sessile.
*Average leaf length.*—Approximately 2.8 cm.
*Average leaf width.*—Approximately 1.7 cm.
*Average leaflet length.*—Approximately 1.4 cm.
*Average leaflet width.*—Approximately 0.5 cm.
*Shape of leaflet.*—Oblanceolate.
*Leaflet apex.*—Acute to obtuse.
*Leaflet base.*—Cuneate.
*Leaflet margin.*—Entire.
*Leaflet texture of top surface.*—Pubescent.
*Leaflet texture of bottom surface.*—Pubescent.
*Color.*—Young foliage upper side: Near RHS Green 137B. Young foliage under side: Near RHS Green 138C. Mature foliage upper side: Near RHS Green 137B. Mature foliage under side: Near RHS Green 138C.
*Venation.*—Type: Pinnate. Venation color upper side: RHS Green 137D. Venation color under side: RHS 138C.
*Petiole.*—Length: Approximately 5 mm. Diameter: Approximately 1 mm. Texture: Pubescent. Color, upper and lower surfaces: Near RHS Yellow-Green 145B.

FLOWER

Natural flowering season: Plants begin flowering about 8 months after planting and flower from early Summer until late Autumn in Ireland.
Flower arrangement, shape and habit: Single rotate flowers. Flowers usually sub-terminal and in groups of 2 to 4. Flower face upward.
Flower longevity on plant: About 4 days.
Quantity of flowers: About 22 flowers and flower buds per lateral branch.
Flowers persistent or self cleaning: Self-cleaning.
Fragrance: None detected.
Flower size:
*Diameter.*—Approximately 2.6 cm.
*Depth.*—Approximately 2.7 cm.
Petals:
*Petal arrangement.*—5, in a single whorl.
*Margin.*—Entire.
*Apex.*—Obtuse.
*Length.*—Approximately 1.0 cm.
*Width.*—Approximately 1.2 cm.
*Shape.*—Obovate.
*Base.*—Obtuse.
*Texture.*—Smooth, glabrous, upper and lower surfaces.
*Aspect.*—Slight upward cupping.
*Color.*—When opening: Upper surface: Near RHS Yellow 9A. Lower surface: Near RHS Yellow 9C. Fully opened: Upper surface: Near RHS Yellow 9A. Lower surface: Near RHS Yellow 9C.
Bud:
*Shape.*—Ovate.
*Length.*—Average 7 mm.
*Diameter.*—Average 4.5 mm.
*Color.*—Near RHS Green 143B.
Sepals:
*Quantity.*—5, in a single whorl.
*Shape.*—Broad deltate.
*Length.*—Approximately 7 mm.
*Width.*—Approximately 5 mm.
*Margin.*—Entire.
*Apex.*—Acute.
*Base.*—Obtuse.
*Texture.*—Slightly pubescent upper and lower surfaces.
*Color (immature and mature).*—Upper surface: Near Yellow-Green RHS 145A. Lower surface: Near Yellow-Green RHS 145B.
Peduncle:
*Length.*—Average 8 mm.
*Diameter.*—About 1 mm.
*Color.*—Near Yellow-Green RHS 145B.
*Aspect.*—Erect.
*Texture.*—Pubescent.
*Strength.*—Strong.
Pedicels:
*Length.*—Average 3 mm.
*Diameter.*—About 1 mm.
*Color.*—Near Yellow-Green RHS 145B.
*Aspect.*—Erect.
*Texture.*—Pubescent.

REPRODUCTIVE ORGANS

Stamens:
*Number.*—About 20.
*Filament length.*—Approximately 1.5 mm.
*Filament color.*—Near RHS Yellow 9A.
Anthers:
*Shape.*—Ovate.
*Length.*—About 1 mm.

*Color*.—Near RHS Yellow-Orange 22A.

*Pollen*.—Scant.

*Pollen color*.—Near RHS Yellow-Orange 22A.

Pistil:

*Number*.—About 30.

*Length*.—Approximately 5 mm.

*Style*.—Length: Approximately 1 mm. Color: Near RHS Yellow 7A, base Green-White 157A.

*Stigma*.—Shape: Linear. Color: Near RHS Yellow 7A.

Ovary color: Near RHS Green-White 157A.

OTHER CHARACTERISTICS

Seeds and fruits: Not observed to date.

Garden performance: Good.

Disease/pest resistance: Good resistance to powdery mildew. Neither resistance nor susceptibility to pathogens and pests common to *Potentilla* have been observed.

Temperature tolerance: The new variety tolerates temperatures between −31° C. to 38° C.

What is claimed is:

1. A new and distinct cultivar of *Potentilla* plant named 'SMPFMY' as herein illustrated and described.

* * * * *